Feb. 18, 1969 P. A. R. JENSEN Plant Pat. 2,861
THUJA OCCIDENTALIS
Filed Sept. 20, 1966
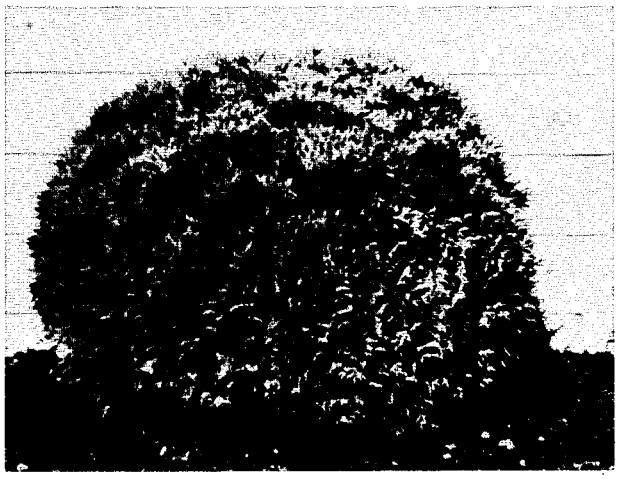
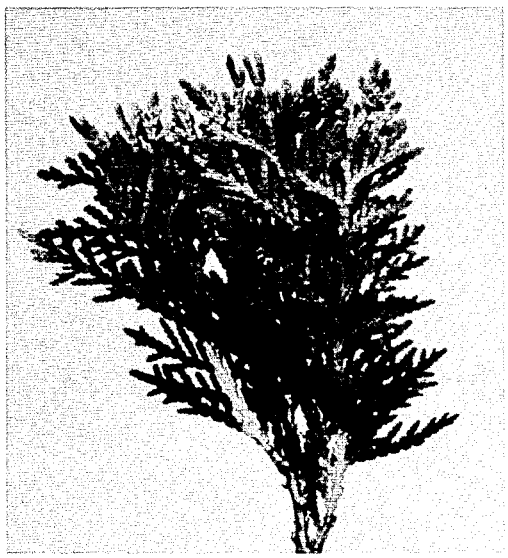
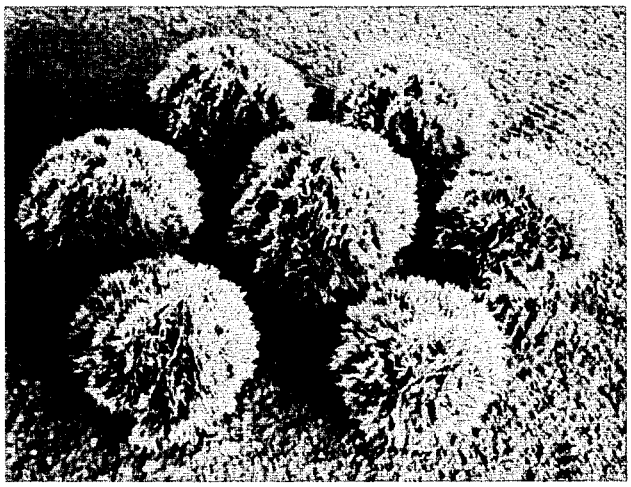

United States Patent Office

Plant Pat. 2,861
Patented Feb. 18, 1969

2,861
THUJA OCCIDENTALIS

Peter Arne Rafael Jensen, Planteskolen, Orting, Denmark

Filed Sept. 20, 1966, Ser. No. 580,841
Claims priority, application Denmark, Sept. 23, 1965, 73
U.S. Cl. Plt.—50 1 Claim
Int. Cl. A01h 7/00

My discovery relates to a new and distinct variety of the evergreen plant of the species *Thuja occidentalis* L., having certain desirable characteristics as an ornamental evergreen.

It was my object to find a pretty Thuja of characteristic dense and regular growth, suitable for planting in cemeteries, in front gardens and at other places where only very low vegetation is permissible or desirable. Further, such a Thuja was to have a resistance to weather conditions and diseases equal to that of the cultivar hitherto known.

In 1947 I purchased a consignment of seeds of *Thuja occidentalis,* assuming that the seeds had been harvested from ordinary hedge plants of *Thuja occidentalis.* The seeds were planted in the spring of 1948, but at the stage to which the plants had developed a couple of years later I found that the seeds must have been picked in an area with a large variety of garden forms of Thuja, the seedlings here showing distinct characteristics that must originate from crossings between different types normally grown in gardens and parks only.

In 1952 about 2000 of these plants, many of them of a characteristic habit of growth, were planted by me for observation. After a couple of years, however, all those not considered of a form sufficiently distinct from the known forms were rejected, only one of the plants, which by its appearance was distinct from all known types, and simultaneously rather near the ideal of a dwarf form, being made the subject of multiplication.

The new variety is, during the growing period, of a distinct pale green colour and owing to its dwarfish growth it is more fine-needled than conventional forms of *Thuja occidentalis* which it otherwise resembles by the form and structure of its foliage.

The accompanying drawing shows typical specimens of the vegetative growth and foliage of the new variety as depicted in colour as nearly true as it is reasonably possible to make the same in a colour illustration of this character.

The following is a detailed description of the new variety with colour terminology in accordance with the British Horticultural Colour Chart issued by the British Colour Council in collaboration with the Royal Horticultural Society, Banbury, 1942.

The plant is of a distinct dwarf growth, developing more slowly than hitherto known Thuja varieties. The mother plant is now 19 years old and has a height of about 45 cm. and a spread of about 55 cm. Some 11-year plants from cuttings thereof have a height of about 25 cm. and a spread of 30 cm. The mother plant, 7 of the 11-year plants and a branch are shown on the drawings.

When the plant has reached the age of 7–8 years, it is of very regular globular and very compact form. These characteristics are preserved by the plant up through the years.

Its branches are very dense and all of them almost upright, with a very short annual increment. The small branches of the plant are alternate, upright and flat with regular distichous, dense and flat sprays, as they are coming only from needles with flank position.

The older needles and shoots are of the colour Spinach Green (Plate 960/1–2); young shoots and needles are Lettuce Green (Plate 861/1). They are dull or slightly glossy and somewhat darker at the edge of the needles.

The distinctive difference of colour between upper and underside as known from branches of *Thuja occidentalis* is of limited and rare occurrence in the new variety, the branches of which are all nearly fully upright. Owing to the compact form of the plant very little light penetrates through the branches.

Both sides of the branches are in the most cases of uniform colour. Only small twigs, which are slightly horizontal, are of a lighter colour on the underside, more greyish green (Plate 860/2–3), Scheeles Green. In winter the needles grow slightly brownish-green as in the species.

The needles are evergreen and scalelike, short and thin, and being smaller they are thus finer than those of the species, but otherwise not differing from same, the fragrance corresponding likewise to that which is characteristic of *Thuja occidentalis.*

No flowers nor cones have been observed so far on the new variety.

Its roots are long and dense and very substantially branched.

*Cultivation.*—The new variety seems to be like the species in regard to requirements of cultivation and it is able to grow on all ordinary cultivated lands. It develops substantially under full sunshine and slightly shaded conditions, but not quite as well in deep shade.

*Reproduction.*—As the mother plant has not yet produced any seeds, the only practical possibility of multiplication consists in its propagation vegetatively. This may very well be accomplished by means of cuttings like other Thuja plants and healthy and vigorous cuttings from the now 19 year old original plant may still be taken. However, the original plant is being preserved now and propagative material is being taken from the numerous plants developed from cuttings of previous years, as a rule from 4 to 6 year old plants.

The plants have so far been found to be healthy, though in a few cases a slight attack by a fungus, *Pestalotia funerea* Desm., has been ascertained on the branches in the middle of the plant. However, the said attack seems not to be of any essential importance.

*Use.*—The new variety of *Thuja occidentalis* is well suited for cultivation everywhere in low beds and rockeries and in particular it is suitable for planting in cemeteries and at other places where slow growth is desired.

I claim:

1. A new and distinct variety of the *Thuja occidentalis* substantially as herein shown and described, characterised particularly as to novelty by its very regularly globular and compact form, its slow and regular dwarf growth and during the growing period the distinctive pale green colour of its very fine-needled foliage, in addition to the very little difference in colour between the upper and underside of its branches.

References Cited

Mayfair Nurseries catalog for 1961, p. 4 relied on.

Morton Arboretum Bull. of Popular Information, February-March 1962, p. 8 relied on.

Girard Nurseries cat. for 1963, p. 14 relied on.

Kelsey Nursery Service catalog for spring 1963, p. 35 relied on.

ROBERT E. BAGWILL, *Primary Examiner.*